`US007125709B2`

United States Patent
Tanaka et al.

(10) Patent No.: US 7,125,709 B2
(45) Date of Patent: Oct. 24, 2006

(54) CULTURE DEVICE AND METHOD FOR EUKARYOTIC CELL TRANSFECTION

(75) Inventors: Yasunobu Tanaka, San Diego, CA (US); Lei Yu, Carlsbad, CA (US); Shouping Ji, Vista, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 10/775,341

(22) Filed: Feb. 10, 2004

(65) Prior Publication Data

US 2005/0176132 A1    Aug. 11, 2005

(51) Int. Cl.
*C12M 1/00* (2006.01)
*C12M 1/16* (2006.01)

(52) U.S. Cl. .................. 435/285.1; 435/6; 435/29; 435/455; 435/468; 435/304.1; 435/305.1

(58) Field of Classification Search ............ 435/289.1, 435/304.1, 304.3, 305.1, 305.2, 285.1
See application file for complete search history.

(56) References Cited

U.S. PATENT DOCUMENTS

| | | | |
|---|---|---|---|
| 5,861,306 A | | 1/1999 | Pugh et al. |
| 6,544,790 B1 | | 4/2003 | Sabatini |
| 6,670,129 B1 | * | 12/2003 | Webb et al. .................. 435/6 |
| 2002/0006664 A1 | * | 1/2002 | Sabatini ..................... 435/456 |
| 2005/0079159 A1 | * | 4/2005 | Shastri et al. .............. 424/93.7 |

OTHER PUBLICATIONS

Ausubel et al, eds. Current Protocols in Molecular Biology, 1988, John Wiley & Sons, vol. 1, Unit 9.1, pp. 9.1.1-9.1.4.*
Qiagen Inc., "Effecten Transfection Reagent" Product Information, Cat. No. 301425, http://www1.qiagen.com/Products/Transfection/TransfectionReagents/EffecteneTransfection.aspx?ShowInfo=1 accessed Apr. 20, 2005.*
International Search Report mailed Feb. 9, 2005 and issued to a related foreign application.

* cited by examiner

*Primary Examiner*—Leon B. Crankford, Jr.
*Assistant Examiner*—Allison M. Ford
(74) *Attorney, Agent, or Firm*—Knobbe, Martens, Olson & Bear, LLP

(57) ABSTRACT

A cell culture device for transfecting a eukaryotic cell is disclosed. The cell culture/transfection device may be a multiwell plate or slide which has been coated with a metal salt such as $CaCl_2$. Methods of using the cell culture device to transfect mammalian cells and/or to monitor cell transfection are described. Kits are also described which include the cell transfection device, eukaryotic cells to be transformed and nucleic acid for transformation.

46 Claims, 7 Drawing Sheets

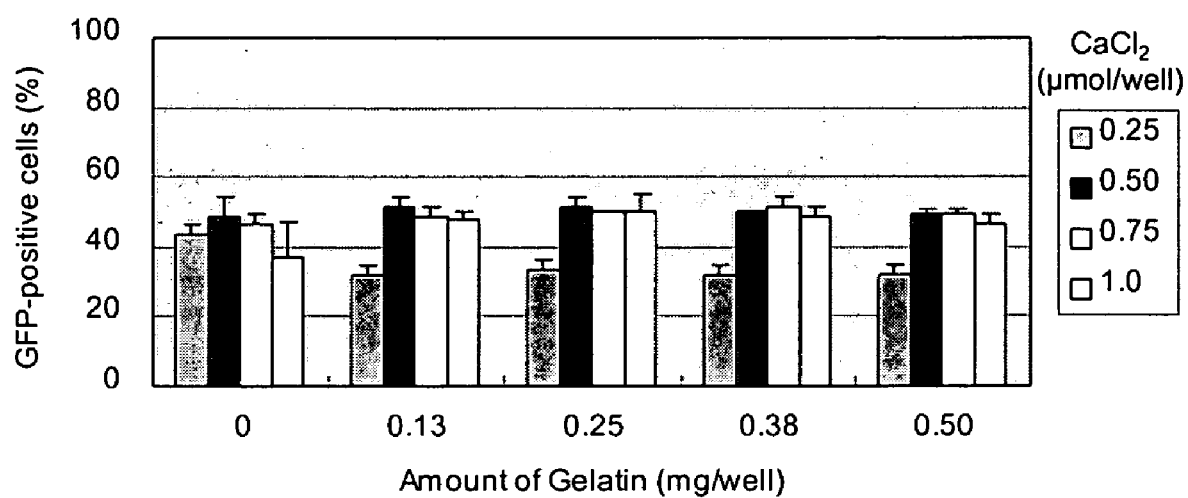
Figure 1  Transfection Efficiency of 293 Cells

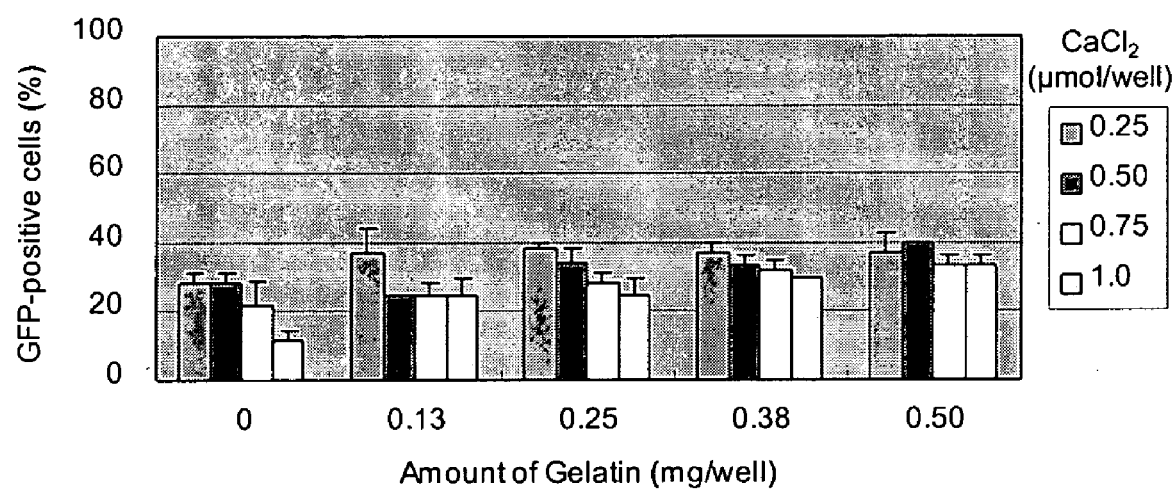
Figure 2 Transfection Efficiency of COS-7 Cells

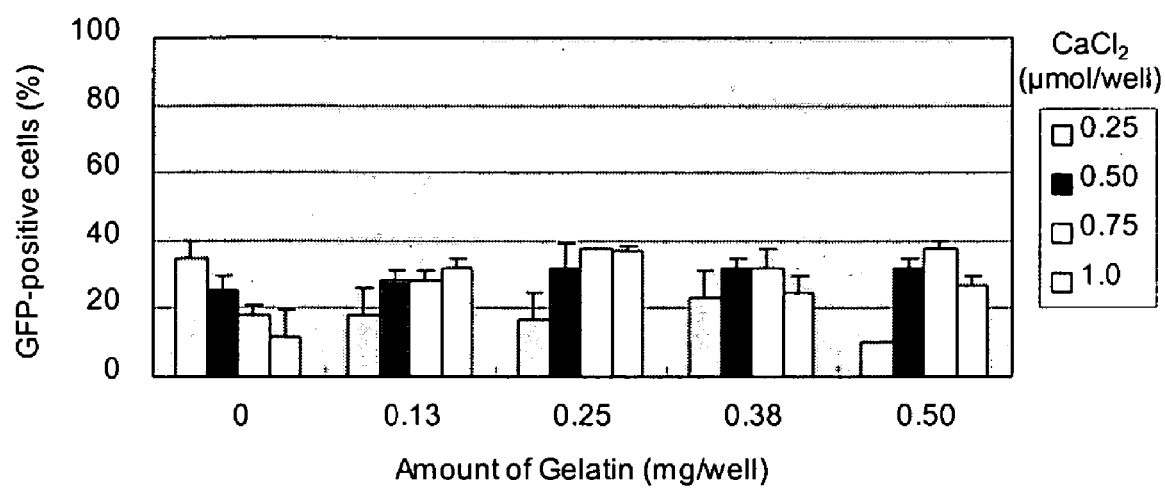
Figure 3 Transfection Efficiency of HeLa Cells

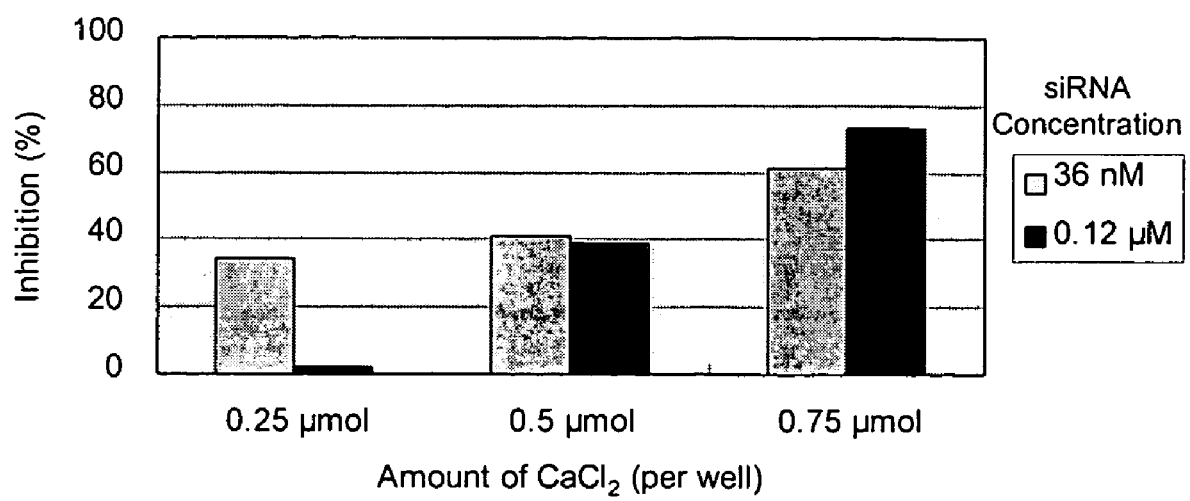
Figure 4  Inhibition of Luciferase Activity by siRNA Delivery

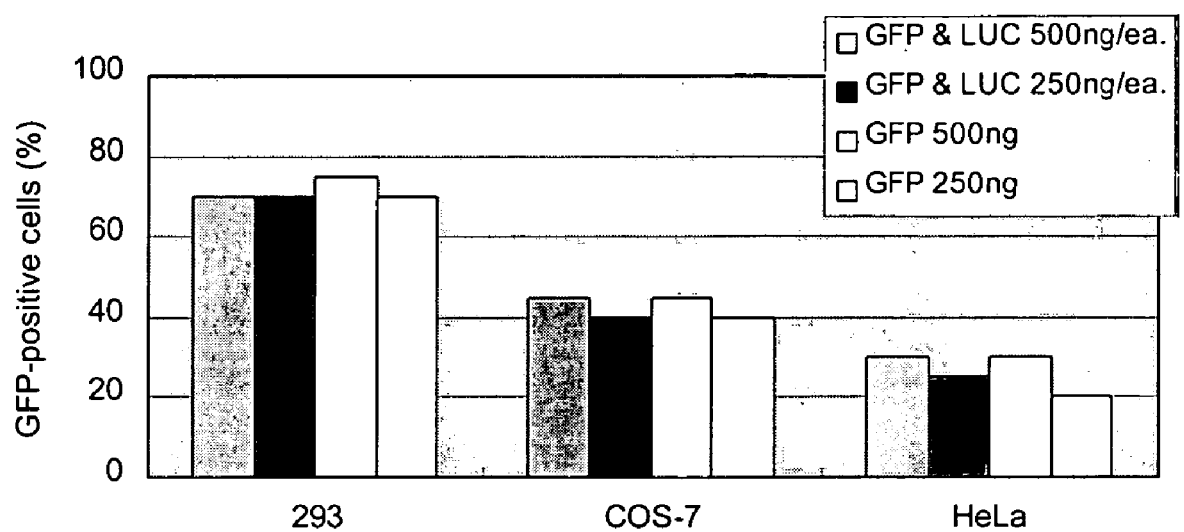
Figure 5 Co-Transfection Efficiency of GFP Plasmid

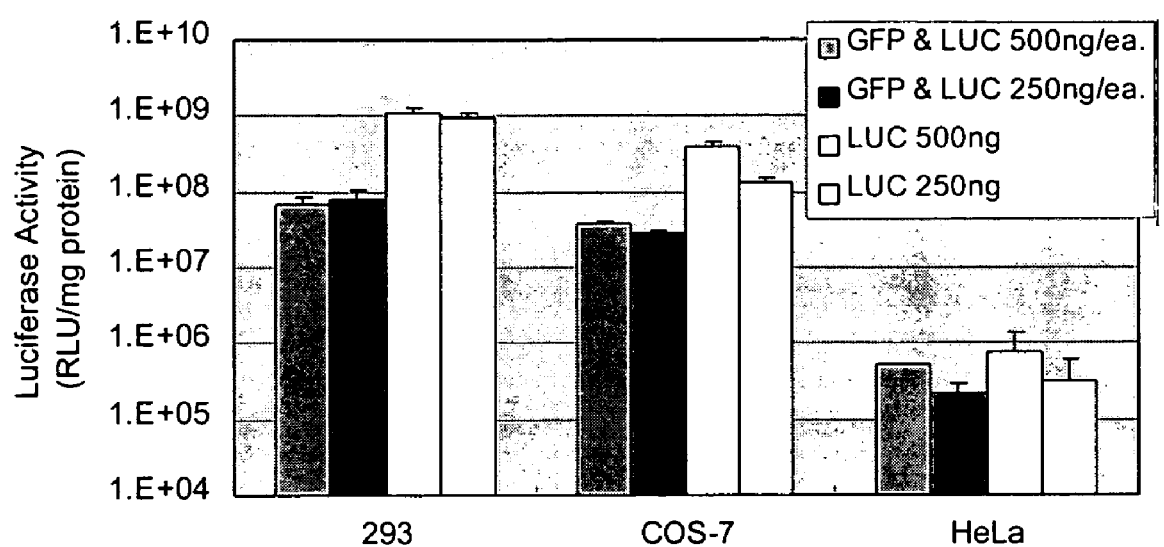
Figure 6  Co-Transfection Efficiency of Luciferase Plasmid

Figure 7   Epifluorescent micrographs of transfected cells
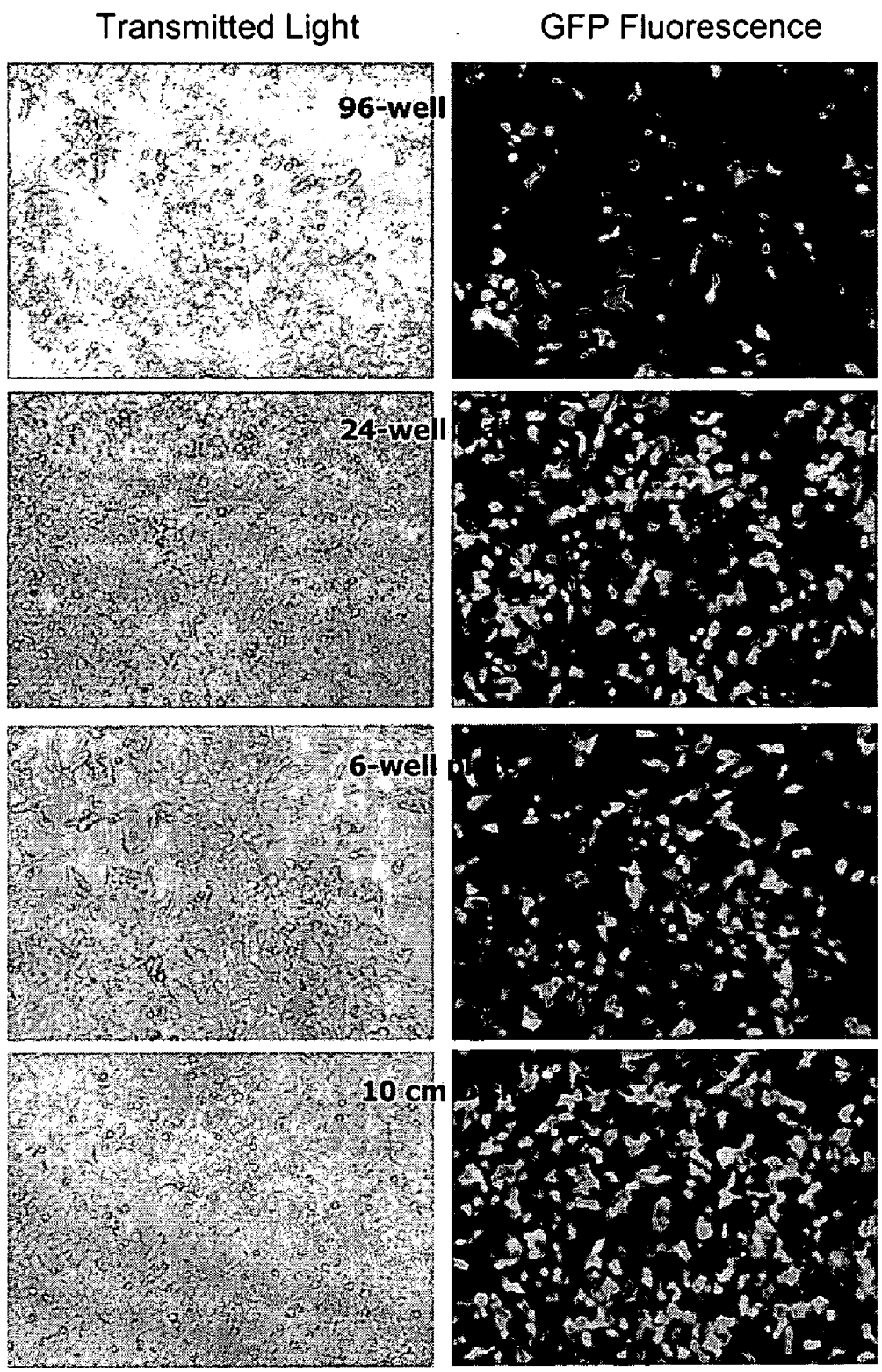

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: sense sequence of siRNA to target GL2
<220> FEATURE:
<221> NAME/KEY: misc_RNA
<222> LOCATION: (1)...(21)
<223> OTHER INFORMATION: first 19 residues are RNA; last 2 residues are
      DNA

<400> SEQUENCE: 1
cguacgcgga auacuucgat t                                              21

<210> SEQ ID NO 2
<211> LENGTH: 21
<212> TYPE: DNA
<213> ORGANISM: Artificial Sequence
<220> FEATURE:
<223> OTHER INFORMATION: antisense sequence of siRNA to target GL2
<220> FEATURE:
<221> NAME/KEY: misc_signal
<222> LOCATION: (1)...(21)
<223> OTHER INFORMATION: first 19 residues are RNA; last 2 residues are
      DNA

<400> SEQUENCE: 2
ucgaaguauu ccgcguacgt t                                              21
```

CULTURE DEVICE AND METHOD FOR EUKARYOTIC CELL TRANSFECTION

BACKGROUND OF THE INVENTION

1. Field of the Invention

In one embodiment, the present invention is directed to a transfection device for eukaryotic cells. In another embodiment, the present invention is directed to kits and formulations for cell transfection which are useful with the transfection device. Methods of cell transfection using the transfection device are also described.

2. Description of the Related Art

Gene transfection methods can be used to introduce nucleic acids into cells and are useful in studying gene regulation and function. High throughput assays that can be used to screen large sets of DNAs to identify those encoding products with properties of interest are particularly useful. Gene transfection is the delivery and introduction of biologically functional nucleic acids into a cell, such as a eukaryotic cell, in such a way that the nucleic acid retains its function within the cell. Gene transfection is widely applied in studies related to gene regulation, gene function, molecular therapy, signal transduction, drug screening, and gene therapy studies. As the cloning and cataloging of genes from higher organisms continues, researchers seek to discover the function of the genes and to identify gene products with desired properties. This growing collection of gene sequences requires the development of systematic and high-throughput approaches to characterizing gene products and analyzing gene function, as well as other areas of research in cell and molecular biology.

Both viral and non-viral gene carriers have been used in gene delivery. Viral vectors have been shown to have higher transfection efficiency than non-viral carriers, but the safety of viral vectors hampers its applicability (Verma I. M and Somia N. *Nature* 389 (1997), pp. 239–242; Marhsall E. *Science* 286 (2000), pp. 2244–2245). Although non-viral transfection systems have not exhibited the efficiency of viral vectors, they have received significant attention, because of their theoretical safety when compared to viral vectors. In addition, viral vector preparation is a complicated and expensive process, which limits the application of viral vectors in vitro. The preparation of non-viral carriers is simpler and more cost effective in comparison to preparation of viral carriers, making synthetic gene carriers desirable as transfection reagents in in vitro studies.

Most non-viral vectors mimic important features of viral cell entry in order to overcome cellular barriers, which are meant to prevent infiltration by foreign genetic material. Non-viral gene vectors, based on a gene carrier backbone, can be classified as a) lipoplexes, b) polyplexes, and c) lipopolyplexes. Lipoplexes are assemblies of nucleic acids with a lipidic component, which is usually cationic. Gene transfer by lipoplexes is called lipofection. Polyplexes are complexes of nucleic acids with cationic polymer. Lipopolyplexes comprise both a lipid and a polymer component. Often such DNA complexes are further modified to contain a cell targeting or an intracellular targeting moiety and/or a membrane-destabilizing component, for example, a viral protein or peptide or a membrane-disruptive synthetic peptide. Recently, bacteria and phages have also been described as shuttles for the transfer of nucleic acids into cells.

Most non-viral transfection reagents are synthetic cationic molecules and have been reported to "coat" the nucleic acid by interaction of the cationic sites on the cation and anionic sites on the nucleic acid. The positively-charged DNA-cationic molecule complex interacts with the negatively charged cell membrane to facilitate the passage of the DNA through the cell membrane by non-specific endocytosis. (Schofield, Brit. Microencapsulated. Bull, 51(1):56–71 (1995)). In most conventional gene transfection protocols, the cells are seeded on cell culture devices 16 to 24 hours before transfection. The transfection reagent (such as a cationic polymer carrier) and DNA are usually prepared in separate tubes, and each respective solution is diluted in medium (containing no fetal bovine serum or antibiotics). The solutions are then mixed by carefully and slowing adding one solution to the other while continuously vortexing the mixture. The mixture is incubated at room temperature for 15–45 minutes to allow the transfection reagent-DNA complexes to form. Prior to transfection, the cell culture medium is removed and the cells are washed with buffer to remove the residues of serum and antibiotics. The solution containing DNA-transfection reagent complexes is added to the cells, and the cells are incubated for about 3–4 hours. The medium containing transfection reagent would then be replaced with fresh medium. The cells would finally be analyzed at one or more specific time point(s). This is obviously a time consuming procedure, particularly when the number of samples to be transfected is very large.

Several major problems exist in conventional transfection procedures. First, conventional procedures are time-consuming, particularly when there are many cell or gene samples to be used in transfection experiments. Also, the results derived from common transfection procedures are difficult to reproduce, due to the number of steps required. For instance, in producing the DNA-transfection reagent, the formation of the complex is influenced by concentration and volume of nucleic acid and reagents, pH, temperature, type of buffer(s) used, length and speed of vortexing, incubation time, and other factors. Although the same reagents and procedure may be followed, different results may be obtained. Results derived from multi-step procedures are often influenced by human or mechanical error or other variations at each step. In addition, refreshing the cell culture medium following transfection disturbs the cells and may cause them to detach from the surface on which they are cultured, thus leading to variation and unpredictability in the final results. Due to all the factors noted, conventional transfection methods require a highly skilled individual to perform the transfection experiment or assay.

Sabatini (U.S. 2002/0006664A1) describes DNA containing a mixture and deposited on a glass slide. However the system only allows transfection with the previously deposited DNA.

U.S. patent application Ser. No. 10/341,059, which is incorporated herein by reference, describes a cell culture/transfection device where the transfection is mediated by a lipid polymer. Some of the methods of application Ser. No. 10/341,059 may be applied to the transfection formulations described herein.

In one aspect of the present invention, a cell culture/transfection device is disclosed which reduces the cost of transfection assays. Transfection with a molecule of interest is accomplished in a simple procedure.

As discussed above, conventional transfection is a lengthy and technically difficult procedure. Generally, three steps are required: 1) cells are seeded in cell culture plate or dish and incubated until sufficient confluence is achieved; 2) transfection reagent/nucleic acid complexes are prepared; and 3) nucleic acids of interest are added along with the transfection reagent and further incubation is carried out. Two incubation periods are needed and typically it takes more than two days to complete all the steps. In contrast, embodiments of the present invention provide a simple procedure that involves only a single incubation step. A cell culture device, which has previously been coated with a transfection reagent, allows transfection by adding the nucleic acid of interest and the cell culture in succession. The transfected cells may then be cultured in the same device. Thus the cells may be transfected and cultured in the cell culture device without the need for further manipulation of the cells immediately after the transfection step. Transfection efficiency is comparable to regular transfection. Consequently, this invention provides an easy transfection procedure and reduces the time required for the transfection procedure by more than one day. Large numbers of cells may be transfected efficiently.

SUMMARY OF THE INVENTION

Certain embodiments are directed to a multiwell plate for transfecting a eukaryotic cell wherein the bottom of at least some of the wells are at least partially coated with a composition including a metal salt. In preferred embodiments, the metal salt is a calcium salt. In more preferred embodiments, the calcium salt is either calcium chloride or calcium acetate.

In some preferred embodiments, the multiwell plate includes a matrix complex. Preferably, the composition including a metal salt is retained on the multiwell plate. More preferably, the composition is retained on the multiwell plate with a matrix complex. In more preferred embodiments, the matrix complex is selected from proteins, glycoproteins, peptides, polysaccharides, and polymers or combinations thereof. In some preferred embodiments, the protein is gelatin, collagen, laminin, fibronectin, or bovine serum albumin or a combination thereof. In preferred embodiments, the polymer is selected from hydrogels, biodegradable polymers, and biocompatible materials.

Certain embodiments of the invention are directed to a cell culture/transfection device for transfecting a eukaryotic cell, including a solid surface, wherein the solid surface is coated with calcium chloride in a gel matrix. In preferred embodiments, the surface may be a continuous surface, flasks, dishes, tubes, multi-well plates, slides, or implanted devices. In preferred embodiments, the solid surface is glass, polystyrene or epoxy resin. In most preferred embodiments, the solid surface is either a slide or a multi-well plate.

Certain embodiments of the invention are directed to a kit which includes the cell transfection device discussed above for transfecting a eukaryotic cell, including a solid surface, wherein the solid surface is coated with calcium chloride in a gel matrix, eukaryotic cells to be transformed, and nucleic acid for transformation. In preferred embodiments, the eukaryotic cells are mammalian cells. Preferably, the eukaryotic cells may be dividing cells or non-dividing cells. Preferably, the eukaryotic cells are transformed cells or primary cells. Preferably, the eukaryotic cells are somatic or stem cells. In some preferred embodiments, the eukaryotic cell is a plant cell. In alternate preferred embodiments, the eukaryotic cell is an insect cell.

In preferred embodiments, the kit includes at least one nucleic acid which is selected from DNA, RNA, DNA/RNA hybrid and chemically modified nucleic acids. More preferably, the chemically modified nucleic acid includes a peptide nucleic acid. More preferably, the DNA is circular, linear, or single strand oligonucleotide. More preferably, the RNA is single stranded or double stranded. Yet more preferably, the single-stranded RNA is a ribozyme. Yet more preferably, the double-stranded RNA is siRNA.

Certain embodiments of the invention are directed to a method for transfection of eukaryotic cells which includes the steps of providing a solid surface at least partially coated with a composition including a metal salt, adding at least one nucleic acid or at least one polypeptide to be introduced into the eukaryotic cell onto the solid surface, and seeding eukaryotic cells onto the solid surface at a sufficient density and under appropriate conditions for introduction of the nucleic acids or polypeptides into the eukaryotic cells. Preferably, the surface is selected from flasks, dishes, tubes, continuous surface, multi-well plates, slides, and implanted devices. Preferably, the solid surface is glass, polystyrene or epoxy resin.

In preferred embodiments, the metal salt is a calcium salt. More preferably, the calcium salt is calcium chloride or calcium acetate.

In preferred embodiments, the composition including a metal salt also includes a matrix complex. Preferably, the composition is retained on the solid surface. More preferably, the composition is retained on the solid surface with a matrix complex. In yet more preferred embodiments, the matrix complex is selected from proteins, glycoproteins, peptides, polysaccharides, and polymers or combinations thereof. Most preferably, the protein is selected from gelatin, collagen, laminin, fibronectin, and bovine serum albumin or a combination thereof. Most preferably, the polymer is selected from hydrogels, biodegradable polymers, and biocompatible materials.

In more preferred embodiments, the solid surface is either a slide or a multi-well plate.

In preferred embodiments, the eukaryotic cells are mammalian cells. In preferred embodiments, the eukaryotic cells are dividing cells or non-dividing cells. In preferred embodiments, the eukaryotic cells are transformed cells or primary cells. In preferred embodiments, the eukaryotic cells are somatic or stem cells. More preferably, the eukaryotic cell is a plant cell. In an alternate more preferred embodiment, the eukaryotic cell is an insect cell.

In preferred embodiments of the method, at least one nucleic acid is added which is selected from DNA, RNA, DNA/RNA hybrid and chemically modified nucleic acids. More preferably, the chemically modified nucleic acid includes a peptide nucleic acid. More preferably, the DNA is circular, linear, or single strand oligonucleotide. More preferably, the RNA is single stranded or double stranded. In a most preferred embodiment, the single-stranded RNA is a ribozyme. In another most preferred embodiment, the double-stranded RNA is siRNA.

Certain embodiments of the invention are directed to a method of determining whether a biomolecule can enter a cell which includes the steps of:
(a) providing a solid surface coated with a polymer or lipid to which said biomolecule can interact;
(b) adding the biomolecules to the solid surface such that the biomolecules interact with said polymer or lipid;
(c) seeding cells onto the surface with sufficient density and under appropriate conditions for introduction of the biomolecules into the cells; and
(d) detecting whether the biomolecule has been delivered to the cells.

In preferred embodiments, the biomolecules added to the solid surface are nucleic acids, proteins, peptides, sugars, polysaccharides, or organic compounds. More preferably, the nucleic acids are DNA, RNA, DNA/RNA hybrid or chemically modified nucleic acids. Most preferably, the chemically modified nucleic acid includes a peptide nucleic acid. Most preferably, the DNA is circular, linear, or single strand oligonucleotide. Preferably, the RNA is single stranded or double stranded. Most preferably, the single-stranded RNA is a ribozyme. Most preferably, the double-stranded RNA is siRNA.

In preferred embodiments, the cells seeded onto the surface are mammalian cells. Preferably, the cells are dividing cells or non-dividing cells. Preferably, the cells are transformed cells or primary cells. Preferably, the cells are somatic or stem cells. More preferably, the cell is a plant cell. In an alternate more preferred embodiment, the cell is an insect cell.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

FIG. 1 shows transfection efficiencies for 293 cells assayed at 0–0.5 mg gelatin/well and 0.25–1.0 µmol $CaCl_2$/well using GFP as reporter.

FIG. 2 shows transfection efficiencies for COS-7 cells assayed at 0–0.5 mg gelatin/well and 0.25–1.0 µmol $CaCl_2$/well using GFP as reporter.

FIG. 3 shows transfection efficiencies for HeLa cells assayed at 0–0.5 mg gelatin/well and 0.25–1.0 µmol $CaCl_2$/well using GFP as reporter.

FIG. 4 shows inhibition of Luciferase activity by siRNA delivery at 0.25 µmol, 0.5 µmol, and 0.75 µmol $CaCl_2$ concentrations and 36 nM and 0.12 µM concentration of siRNA.

FIG. 5 shows efficiencies for co-transfection using GFP plasmid as assayed in three different cell types: 293, COS-7, and HeLa cells.

FIG. 6 shows efficiencies for co-transfection using luciferase plasmid as assayed in three different cell types: 293, COS-7, and HeLa cells.

FIG. 7 shows epifluorescent micrographs of transfected cells in both small scale (96-well plates and 24-well plates) and large scale (6 well plates and 10 cm dishes) applications. Transmitted light is shown on the left panels and the fluorescence from GFP is shown in the right hand panels.

DETAILED DESCRIPTION OF THE PREFERRED EMBODIMENT

A novel transfection device and method are described herein which is simple, convenient, and efficient compared to conventional transfection assays. A transfection device is made according to methods described herein by affixing a transfection reagent on the solid surface of a cell culture device. By using this device, researchers need only add a nucleic acid or other biomolecule carrier system to the surface of the cell culture device. There is no need to pre-mix the DNA or biomolecule with a transfection reagent. This removes a key timing-consuming step, which is required by conventional transfection procedures. Scientists only require approximately 40 minutes to complete the entire transfection process for 10 samples, compared to 2 to 5 hours or more required by current methods. This is particularly favorable for high throughput transfection assays, in which hundreds of samples will be tested at a time.

As compared to conventional transfection, there are several advantages to the new method described herein. It provides a transfection device that is very easy to store, and it provides a simple method for biomolecule delivery or gene transfection in which no biomaterial/transfection reagent mixing step is required. The transfection procedure described herein can be finished in a short period of time, for instance approximately 40 minutes, and it provides a high throughput method for transfection or drug delivery in which large numbers of samples may be transfected at a time.

Embodiments of the method and device for gene delivery which are described herein overcome the common problems encountered in conventional transfection assays described above. Transfection reagents are simply coated onto the surface of a cell culture device, which can be easily commercialized and mass-produced. Customers, researchers for instance, need only add a biomolecule, such as a nucleic acid of interest, directly to the surface of a cell culture device in order to prepare the device prior to transfection. Cells are then seeded on the surface of the cell culture device and incubated, without changing the medium, and the cells are analyzed. Changing medium during the transfection procedure is unnecessary. The methods described herein dramatically reduce the risk of error, by reducing the number of steps involved, thus increasing consistency and accuracy of the system.

According to the methods described herein, transfection reagents were affixed on the surface of a slide, multi-well plate, or other surface to form a transfection device. By using this device, people need only add DNA or other biomolecule to the surface and allow the transfection reagent to form a complex with the DNA or biomolecule. This reaction occurs in approximately 30 minutes, then cells are seeded on the surface and incubated under suitable conditions for introduction of the biomolecule(s) into the cells.

Any suitable surface that can be used to affix the nucleic acid/biomolecule-containing mixture to its surface can be used. For example, the surface can be glass, plastics (such as polytetrafluoroethylene, polyvinylidenedifluoride, polystyrene, polycarbonate, polypropylene), silicon, metal, (such as gold), membranes (such as nitrocellulose, methylcellulose, PTFE or cellulose), paper, biomaterials (such as protein, gelatin, agar), tissues (such as skin, endothelial tissue, bone, cartilage), minerals (such as hydroxylapatite, graphite). According to preferred embodiments the surfaces may be slides (glass or poly-L-lysine coated slides) or wells of a multi-well plate.

For slides, such as a glass slide coated with poly-L-lysine (e.g., Sigma, Inc.), the transfection reagents are fixed on the surface and dried, and then a nucleic acid of interest or a nucleic acid to be introduced into cells, a protein, peptide, or small molecule drug is introduced. The slide is incubated at room temperature for 30 minutes to form biomolecule/transfection reagent complexes on the surface of the transfection device. The biomolecule/transfection reagent complexes create a medium for use in high throughput microarrays, which can be used to study hundreds to thousands of nucleic acids, proteins, peptides and other small molecular drugs at the same time. In an alternative embodiment, the transfection reagents or drug delivery reagents can be affixed on the surface of the transfection device in discrete, defined regions to form a microarray of transfection reagents or drug delivery reagents. In this embodiment, molecules, such as nucleic acids, which are to be introduced into cells, are spread on the surface of the transfection device along with a transfection or delivery reagent. This method can be used in screening transfection reagents or other delivery reagents from thousands of compounds. The results of such a screening method can be examined through computer analysis.

In another embodiment of the invention one or more wells of a multi-well plate may be coated with a transfection or drug delivery reagent. Plates commonly used in transfection and drug screening are 96-well and 384-well plates. The transfection or biomolecule delivery reagent can be evenly applied to the bottom of plate. Hundreds of nucleic acids, proteins, peptides or other biomolecules are then added into the well(s) by, for instance, a multichannel pipette or automated machine. Results of transfection are then determined by using a microplate reader. This is a very convenient method of analyzing the transfected cells, because microplate readers are commonly used in most biomedical laboratories. The multi-well plate coated with transfection or biomolecule delivery reagent can be widely used in most laboratories to study gene regulation, gene function, molecular therapy, and signal transduction, as well as drug screening. Also, if different kinds of transfection reagents are coated on the different wells of multi-well plates, the plates can be used to screen many transfection or delivery reagents relatively efficiently. Recently, 1,536 and 3,456 well plates have been developed, which may also be used according to the methods described herein.

The transfection reagent or delivery reagent are preferably metal salts which can introduce biomolecules, such as nucleic acids, proteins, peptides, sugars, polysaccharides, organic compounds, and other biomolecules into cells. Preferred embodiments use calcium metal salts, particularly calcium chloride or calcium acetate.

According to an one embodiment, the transfection or delivery reagent can be mixed with a matrix, such as proteins, peptides, polysaccharides, or other polymers. The protein can be gelatin, collagen, bovine serum albumin or any other protein that can be used in affixing proteins to a surface. The polymers can be hydrogels, copolymers, non-degradable or biodegradable polymers and biocompatible materials. The polysaccharide can be any compound that can form a membrane and coat the delivery reagent, such chitosan. Other reagents, such as cytotoxicity reductive reagents, cell binding reagents, cell growing reagents, cell stimulating reagents or cell inhibiting reagents and the compounds for culturing specific cells, can be also affixed to the transfection device along with the transfection or delivery reagent.

According to another embodiment, a gelatin-transfection reagent mixture, comprising transfection reagent (e.g., metal salt such as calcium chloride) and gelatin that is present in an appropriate solvent, such as water or double deionized water, may be affixed to the transfection device. In a further embodiment a cell culture reagent may also be present in the gelatin-transfection reagent mixture. The mixture is evenly spread onto a surface, such as a slide and multi-well plate, thus producing a transfection surface bearing the gelatin-transfection reagent mixture. In alternative embodiments, different transfection reagent-gelatin mixtures may also be spotted on discrete regions on the surface of the transfection device. The resulting product is allowed to dry completely under suitable conditions such that the gelatin-transfection reagent mixture is affixed at the site of application of the mixture. For example, the resulting product can be dried at specific temperatures or humidity or in a vacuum-dessicator.

The concentration of transfection reagent present in the mixture depends on the transfection efficiency and cytotoxicity of the reagent. Typically there is a balance between transfection efficiency and cytotoxicity. At concentrations in which a transfection reagent is most efficient, while keeping cytotoxicity at an acceptable level, the concentration of transfection reagent is at the optimal level. The concentration of transfection reagent will generally be in the range of about 1 to 10 mM, preferably about 2–7 mM. Similarly, the concentration of gelatin or other matrix depends on the experiment or assay to be performed, but the concentration will generally be in the range of 0.1% to 5%, preferably 0.5 to 2% and most preferably about 1–2% of the transfection reagent. According to embodiments shown in the examples, the gelatin concentration is about 2% of the transfection reagent. Of course, the concentration of the transfection reagent in the gel matrix will be higher than in the total reaction volume—on the order of 5 mM to 0.1M, preferably 10–40 mM. In a preferred embodiment, the transfection agent in the matrix is applied to the transfection device and allowed to dry in a clean atmosphere. Preferably, the transfection agent in the matrix is dried for two hours to overnight in a sterile hood.

The molecules to be introduced into cells can be nucleic acids, proteins, peptides, peptide nucleic acid (PNA) and other biomolecules. The nucleic acid can be DNA, RNA and DNA/hybrid, etc. If the DNA used is present in a vector, the vector can be of any type, such as a plasmid (e.g. example, pCMV-GFP, pCMV-luc) or viral-based vector(e.g. pLXSN). The DNA can also be linear fragment with a promoter sequence (such CMV promoter) at the 5' end of the cDNA to be expressed and a poly A site at the 3' end. These gene expression elements allow the cDNA of interest to be transiently expressed in mammalian cells. If the DNA is the single strand oligodeoxynucleotide (ODN), for example antisense ODN, it can be introduced into cells to regulate target gene expression. In embodiments using RNA the nucleic acid may be single stranded (antisense RNA and ribozyme) or double stranded (RNA interference, siRNA). In most cases, the RNA is modified in order to increase the stability of RNA and improve its function in down regulation of gene expression. In peptide nucleic acid (PNA), the nucleic acid backbone is replaced by peptide, which makes the molecule more stable. In particular embodiments the methods described herein can be used to introduce proteins, peptides and other molecules into cells for various purposes, for example molecular therapy, protein function studies, or molecule mechanism studies.

Under appropriate conditions, the biomolecules are added into the transfection device, which has been coated with transfection or delivery reagent(s), to form biomolecule/delivery reagent complexes. The biomolecules are preferably dissolved in cell culture medium without fetal bovine serum and antibiotics, for example Dulbecco's Modified Eagles Medium (DMEM) or opti-MEM. If the transfection or delivery reagent is evenly affixed on the slide, the biomolecules can be spotted onto discrete locations on the slide. Alternatively, transfection or delivery reagents may be spotted on discrete locations on the slide, and the biomolecules can simply be added to cover the whole surface of the transfection device. If the transfection reagent or delivery reagent are affixed on the bottom of multi-well plates, the biomolecules are simply added into different wells by multi-channel pipette, automated device, or other method. The resulting product (transfection device coated with transfection or delivery reagent and biomolecules) is incubated to form the bio-molecule/transfection reagent (or delivery reagent) complexes. In some embodiments, the incubation is for approximately 25 minutes room temperature. In some cases, for example, different kinds of biomolecules are spotted at discrete locations on the slide, and the DNA solution will be removed after incubation to produce a surface bearing biomolecules in complex with transfection reagent. In other embodiments, the biomolecule solution can be kept on the surface.

After adding the biomolecule, cells in an appropriate medium and appropriate density are plated onto the surface. The resulting product (a surface bearing biomolecules and plated cells) is maintained under conditions that result in entry of the biomolecules into plated cells.

Suitable cells for use according to the methods described herein include prokaryotes, yeast, or higher eukaryotic cells, including plant and animal cells, especially mammalian cells. Eukaryotic cells, such as mammalian cells (e.g., human, monkey, canine, feline, bovine, or murine cells), bacterial, insect or plant cells, are plated onto the transfection device, which is coated with transfection or delivery reagent and biomolecules, in sufficient density and under appropriate conditions for introduction/entry of the biomolecule into the eukaryotic cells and either expression of the DNA or interaction of the biomolecule with cellular components. In particular embodiments, the cells may be selected from hematopoietic cells, neuronal cells, pancreatic cells, hepatic cells, chondrocytes, osteocytes, or myocytes. The cells can be fully differentiated cells or progenitor/stem cells.

In preferred embodiments, eukaryotic cells are grown in Dulbecco's Modified Eagles Medium (DMEM) containing 10% heat-inactivated fetal bovine serum (FBS) with L-glutamine and penicillin/streptomycin (pen/strep). It will be appreciated by those of skill in the art that certain cells should be cultured in a special medium, because some cells need special nutrition, such as growth factors and amino acids. The optimal density of cells depends on the cell types and the purpose of experiment. For example, a population of 70–80% confluent cells is preferred for gene transfection, but for oligonucleotide delivery the optimal condition is 30–50% confluent cells. In an example embodiment, if $5 \times 10^4$ 293 cells/well were seeded onto a 96 well plate, the cells would reach 90% confluency at 18–24 hours after cell seeding. For HeLa 705 cells, only $1 \times 10^4$ cells/well are needed to reach a similar confluent percentage in a 96 well plate.

After the cells are seeded on the surface containing biomolecules/delivery reagent, the cells are incubated under optimal conditions for the cell type (e.g. 37° C., 5–10% $CO_2$). The culture time is dependent on the purpose of experiment. Typically, the cells are incubated for 24 to 48 hours for cells to express the target gene in the case of gene transfection experiments. In the analysis of intracellular trafficking of biomolecules in cells, minutes to several hours of incubation may be required and the cells can be observed at defined time points.

The results of biomolecule delivery can be analyzed by different methods. In the case of gene transfection and antisense nucleic acid delivery, the target gene expression level can be detected by reporter genes, such as green fluorescent protein (GFP) gene, luciferase gene, or β-galactosidase gene expression. The signal of GFP can be directly observed under a fluorescence microscope, the activity of luciferase can be detected by a luminometer, and the blue product catalyzed by β-galactosidase can be observed under microscope or determined by a microplate reader. One of skill in the art is familiar with how these reporters function and how they may be introduced into a gene delivery system. The nucleic acid and its product, the protein, peptide, or other biomolecules delivered according to methods described herein and the target modulated by these biomolecules can be determined by various methods, such as detecting immunofluorescence or enzyme immunocytochemistry, autoradiography, or in situ hybridization. If immunofluorescence is used to detect expression of an encoded protein, a fluorescently labeled antibody that binds the target protein is used (e.g., added to the slide under conditions suitable for binding of the antibody to the protein). Cells containing the protein are then identified by detecting a fluorescent signal. If the delivered molecules can modulate gene expression, the target gene expression level can also be determined by methods such as autoradiography, in situ hybridization, and in situ PCR. However, the identification method depends on the properties of the delivered biomolecules, their expression product, the target modulated by it, and/or the final product resulting from delivery of the biomolecules.

EXAMPLES

Example 1

Preparation of Cell Culture/Transfection Device

Calcium chloride and linear polyethylene imine (L-PEI) were used for transfecting plasmid DNA into mammalian cells in vitro to evaluate the transfection efficiency. The transfection reagents were affixed on the well bottoms of a 96-well cell culture plate (Corning Costar, Cat. No. 3997) with gelatin (Type B; SIGMA-ALDRICH, Cat. No. G-9391). In the case of calcium chloride, 0.5 μmol/well of calcium chloride was affixed with 0.5 mg/well of gelatin. In the case of PEI, 3.5 μg/well of PEI was affixed with 0.05 mg/well of gelatin. These reagents and gelatin were dissolved in 25 μl of deionized water (per each well) and distributed to the wells. The wells were then air-dried.

Example 2

Transfection with Cell Culture/Transfection Device for 293 Cells 50 ng of pCMV-GFP plasmid in 25 μl of opti-MEM I (Invitrogen, Cat. No. 31985-070) was added in each well and kept at room temperature for 25 minutes. Next, $5 \times 10^4$ of 293 cells in 100 μl of Dulbecco's modified Eagle Medium (DMEM) (Invitrogen, Cat. No. 11965-084) with 10% calf serum (Invitrogen) were added and incubated at 37° C. in 7.5% $CO_2$. After 24 h incubation, transfection efficiency was estimated by observing GFP fluorescence by using an epifluorescent microscope (IX70, Olympus).

Transfection efficiencies are shown in Table 1. Both transfection reagents were applicable to the transfection system of this invention and showed very high transfection efficiency.

TABLE 1

Transfection Efficiency with Transfectable Cell Culture Device

| Transfection Reagent | GFP-positive cells |
|---|---|
| L-PEI | 60% |
| $CaCl_2$ | 70% |

Example 3

Conventional Transfection for 293 Cells

100 μl of 293 cell culture (5×10$^5$ cells/ml in DMEM) was seeded in a 96-well plate and incubated at 37° C. in 7.5% $CO_2$ for 24 h. After the cultivation, pCMV-GFP plasmid-transfection reagent mixture (final concentration: plasmid; 10 ng/μl, transfection reagent; as written in Table 2), dissolved in opti-MEM, was prepared and incubated at room temperature for 15 min to allow forming plasmid-transfection reagent complex. Then, 15 μl of plasmid-transfection reagent complex was added in each well and incubated at 37° C. in 7.5% $CO_2$ for 24 h. Transfection efficiency was estimated as described in Example 2. As a result, L-PEI was effective in conventional method; however, calcium chloride was not suitable. In the conventional method, two incubation steps and a complicated preparation are required.

As can be seen from Table 2, $CaCl_2$ was not an effective transfection agent when used in a conventional method. L-PEI was an effective agent although transfection efficiencies were lower than observed in the experiment of Example 2 (Table 1).

TABLE 2

Transfection Efficiency in Conventional Protocol

| Transfection Reagent | Amount (per each well) | GFP-positive cells |
|---|---|---|
| L-PEI | 4.8 μg | 35% |
|  | 2.4 μg | 40% |
|  | 1.2 μg | 40% |
|  | 0.60 μg | 30% |
| $CaCl_2$ | 0.38 μmol | 1% |
|  | 0.28 μmol | 0% |
|  | 0.19 μmol | 0% |
|  | 0.094 μmol | 0% |

Example 4

Multiple Cell Lines Assay

Transfection efficiencies on mammalian cells (293 cells, COS-7 cells and HeLa cells) were measured. A cell culture/transfection device was prepared by affixing calcium chloride and gelatin with various conditions on the bottom of a 96-well plate. Transfection of pCMV-GFP was carried out by following the protocol written in Example 2. However, number of seeded cells was 2×10$^4$ in 100 μl of DMEM with 10% calf serum for COS-7 and HeLa cells, and 5×10$^4$ in 100 μl of DMEM with 10% calf serum for 293 cells.

FIGS. 1, 2 and 3 show the transfection efficiency by using the 96-well transfection plate according to the invention. pCMV-GFP plasmid was transfected into every cell line by using this pretreated plate, and this result shows the applicability of the cell culture/transfection plate for a range of commonly cultured mammalian cell types.

Example 5 siRNA Delivery by Using Cell Culture/Transfection Device siRNA is an important tool in the life science research area to investigate the role of specific genes. The methodology described above for the cell culture/transfection device was applied to siRNA delivery.

GT2-293-LUC cell, which has luciferase gene GL2, was purchased from BD Biosciences Clonetech, Palo Alto, Calif. USA and siRNA was purchased from Dharmacon Inc., Lafayette, Colo. USA. Sequence of siRNA which targeted GL2 is as follows:

```
                                          (SEQ ID NO: 1)
Sense sequence:       CGUACGCGGAAUACUUCGAdTdT (SEQ ID NO: 2)
Antisense sequence:   UCGAAGUAUUCCGCGUACGdTdT
```

These two fragments were annealed to form a double-strand.

The cell culture/transfection device was prepared as follows: 25 μl of 2% gelatin type B plus 10, 20 or 30 mM $CaCl_2$ solution was put in a 96-well plate and dried overnight. Therefore, the bottom of each well was covered with 0.5 mg of gelatin and 0.25, 0.50 or 0.75 μmol of $CaCl_2$. Then, 25 μl of siRNA solution (36 nM or 0.12 μM in opti-MEM) were added in each well and incubated for 25 min. 100 μl of GP2-293-LUC cells (5×10$^5$ cells/ml in DMEM with 10% calf serum) were added and incubated at 37° C. in 7.5% $CO_2$ for 48 h. Luciferase activity of cells were determined by using a Dynex MLX Microtiter® plate luminometer and Luciferase Assay System (Promega Corp. Madison, Wis. USA). The effect of siRNA was evaluated by comparing luciferase activity of transfected cells with untreated cells (FIG. 4). The siRNA interfered with luciferase activity of GP2-293-LUC cells by up to 70%. Thus, the devices of this invention are also applicable to siRNA delivery.

Example 6

Co-transfection by Using Cell Culture/Transfection Device

In typical viral vector production, 2 or more plasmids are transfected into cells. Co-transfection can simulate the efficacy of cell culture/transfection device for viral vector production.

pCMV-luc plasmid, which carries luciferase gene, and pCMV-GFP were co-transfected into mammalian cells. The cell culture/transfection device was prepared as follows: 25 μl of 2% gelatin type B plus 20 mM $CaCl_2$ solution was put into wells of a 96-well plate and dried overnight. Therefore, the bottom of each well was covered with 0.5 mg of gelatin and 0.50 μmol of $CaCl_2$. Then, 25 μl of plasmid solution (in opti-MEM) was added in each well and incubated for 25 min. The amount of plasmids per 25 μl of solution was as follows: (1) 500 ng of pCMV-GFP and 500 ng of pCMV-luc; (2) 250 ng of pCMV-GFP and 250 ng of pCMV-luc; (3) 500 ng of pCMV-GFP; (4) 250 ng of pCMV-GFP; (5) 500 ng of pCMV-luc; and (6) 250 ng of pCMV-luc. Then, 100 μl of cell culture (293 cells: 5×10$^5$ cells/ml, COS-7 cells: 2×10$^5$ cells/ml, HeLa cells: 2×10$^5$ cells/ml in DMEM with 10% calf serum) was added. After 24 h incubation, transfection efficiency was estimated by observing GFP fluorescence and by measuring luciferase activity.

FIGS. 5 and 6 show the transfection efficiencies. Regarding GFP fluorescence, there were no obvious differences between normal (one plasmid) transfection and co-transfection in all cell lines. Luciferase activities of co-transfected 293 cells and COS-7 cells were 10-times lower than normally transfected cells, however, the activities of both co-transfected cells were still very high. These results indicate that the cell culture/transfection device described is applicable to co-transfection. Moreover this device is quite promising to viral vector production.

Example 7

Cell Culture/Transfection Device: Large Scale Applications

Embodiments of the cell culture/transfection device were also prepared for large scale applications. 24-well and 6-well plates are in common use and viral vector production is very important, especially for in vivo studies. For this purpose, transfection may be carried out in large cell culture dishes, for example 10 cm or 25 cm diameter.

The devices were prepared as follows: coating solution, containing 2% gelatin type B and 20 mM $CaCl_2$ in deionized water, was put in each well or dish. The amount of coating solution added was: 1) 25 μl in 96-well plate, 2) 100 μl in 24-well plate, 3) 500 μl in 6-well plate, and 4) 2 ml in μl in 10 cm dish. These plates and dishes were dried in a sterile hood.

After drying, 20 μg/ml of pCMV-GFP, dissolved in opti-MEM, was added to the plates and dishes. The amount of solution was: 1) 25 μl in 96-well plate, 2) 100 μl in 24-well plate, 3) 500 μl in 6-well plate, and 4) 3 ml in μl in 10 cm dish. Then, plates and dishes were kept at room temperature for 25 min. Next, 293 cell culture was added to the plates and dishes, and incubated at 37° C. in 7.5% $CO_2$ for 24 h. Finally, transfection efficiency was estimated by observing GFP fluorescence.

FIG. 7 shows GFP fluorescence of transfected cells. Transfection efficiency was quite high in every plate or dish, and cell condition was also good. This data indicates that methods described herein are compatible with various sizes of cell culture devices.

It will be understood by those of skill in the art that numerous and various modifications can be made without departing from the spirit of the present invention. Therefore, it should be clearly understood that the forms of the present invention are illustrative only and are not intended to limit the scope of the present invention.

---

---

What is claimed is:

1. A multiwell plate for transfecting a eukaryotic cell with a biomolecule wherein the bottoms of at least some of the wells are at least partially affixed with a composition consisting essentially of a transfection agent, wherein the transfection reagent is a metal salt.

2. The multiwell plate of claim 1, wherein the metal salt is a calcium salt.

3. The multiwell plate of claim 2, wherein the calcium salt is selected from the group consisting of calcium chloride and calcium acetate.

4. The multiwell plate of claim 1, wherein the composition further comprises a matrix.

5. The multiwell plate of claim 1, wherein the composition is retained on the multiwell plate.

6. The multiwell plate of claim 4, wherein the matrix is selected from the group consisting of proteins, glycoproteins, peptides, polysaccharides, polymers and combinations thereof.

7. The multiwell plate of claim 6, wherein said protein is selected from the group consisting of gelatin, collagen, laminin, fibronectin, bovine serum albumin and combinations thereof.

8. The multiwell plate of claim 6, wherein said polymer is selected from the group consisting of hydrogels, biodegradable polymers, and biocompatible materials.

9. A method of determining whether biomolecules can enter eukaryotic cells, said method comprising:
(a) providing a multiwell plate according to claim 1;
(b) adding the biomolecules to the multiwell plate such that the biomolecules interact with the metal salt;
(c) seeding the eukaryotic cells onto the multiwell plate with sufficient density and under appropriate conditions for introduction of the biomolecules into the cells; and
(d) detecting whether the biomolecule have entered the cells.

10. The method of claim 9, wherein the biomolecules are selected from the group consisting of nucleic acids, proteins, peptides, sugars, polysaccharides, and organic compounds.

11. The method of claim 10, wherein the nucleic acids are selected from the group consisting of DNA, RNA, DNA/RNA hybrid and chemically modified nucleic acids.

12. The method of claim 11, wherein the chemically modified nucleic acid comprises a peptide nucleic acid.

13. The method of claim 11, wherein the DNA is circular, linear, or single strand oligonucleotide.

14. The method of claim 11, wherein the RNA is single stranded or double stranded.

15. The method of claim 14, wherein the single-stranded RNA is a ribozyme.

16. The method of claim 14, wherein the double-stranded RNA is siRNA.

17. The method of claim 9, wherein the cells are mammalian cells.

18. The method of claim 9, wherein the cells are dividing cells or non-dividing cells.

19. The method of claim 9, wherein the cells are transformed cells or primary cells.

20. The method of claim 9, wherein the cells are somatic or stem cells.

21. The method of claim 9, wherein the cell is a plant cell.

22. The method of claim 9, wherein the cell is an insect cell.

23. A cell culture/transfection device for transfecting a eukaryotic cell, consisting essentially of a solid surface, wherein the solid surface is coated with calcium chloride in a gel matrix, wherein the concentration of the calcium chloride in the gel matrix is 10–40 mM.

24. The cell culture/transfection device of claim 23, wherein the surface is selected from the group consisting of flasks, dishes, tubes, multi-well plates, slides, and implanted devices.

25. The cell culture/transfection device of claim 23, wherein the solid surface is glass, polystyrene or epoxy resin.

26. The cell culture/transfection device of claim 23, wherein the solid surface is selected from the group consisting of a slide and a multi-well plate.

27. A method for transfection of eukaryotic cells comprising:
providing a solid surface according to claim 23;
adding at least one nucleic acid or at least one polypeptide to be introduced into the eukaryotic cell onto the solid surface; and
seeding eukaryotic cells onto the solid surface at a sufficient density and under appropriate conditions for introduction of the nucleic acids or polypeptides into the eukaryotic cells.

28. The method of claim 27, wherein the surface is selected from the group consisting of flasks, dishes, tubes, continuous surface, multi-well plates, slides, and implanted devices.

29. The method of claim 27, wherein the solid surface is glass, polystyrene or epoxy resin.

30. The method of claim 27, wherein the calcium chloride in the gel matrix is retained on the solid surface.

31. The method of claim 27, wherein the matrix is selected from the group consisting of proteins, glycoproteins, peptides, polysaccharides, polymers and combinations thereof.

32. The method of claim 31, wherein said matrix is selected from the group consisting of gelatin, collagen, lamimn, fibronectin, polysaccharides, polymers and combinations thereof.

33. The method of claim 31, wherein said polymer is selected from the group consisting of hydrogels, biodegradable polymers, and biocompatible materials.

34. The method of claim 27, wherein the solid surface is selected from the group consisting of a slide and a multi-well plate.

35. The method of claim 27, wherein the eukaryotic cells are mammalian cells.

36. The method of claim 27, wherein the eukaryotic cells are dividing cells or non-dividing cells.

37. The method of claim 27, wherein the eukaryotic cells are transformed cells or primary cells.

38. The method of claim 27, wherein the eukaryotic cells are somatic or stem cells.

39. The method of claim 27, wherein the eukaryotic cell is a plant cell.

40. The method of claim 27, wherein the eukaryotic cell is an insect cell.

41. The method of claim 27, wherein the at least one nucleic acid is selected from the group consisting of DNA, RNA, DNAIRNA hybrid and chemically modified nucleic acids.

42. The method of claim 41, wherein the chemically modified nucleic acid comprises a peptide nucleic acid.

43. The method of claim 41, wherein the DNA is circular, linear, or single strand oligonucleotide.

44. The method of claim 41, wherein the RNA is single stranded or double stranded.

45. The method of claim 44, wherein the single-stranded RNA is a ribozyme.

46. The method of claim 44, wherein the double-stranded RNA is siRNA.

* * * * *

UNITED STATES PATENT AND TRADEMARK OFFICE
CERTIFICATE OF CORRECTION

PATENT NO.          : 7,125,709 B2                                          Page 1 of 1
APPLICATION NO.  : 10/775341
DATED                   : October 24, 2006
INVENTOR(S)          : Tanaka et al.

It is certified that error appears in the above-identified patent and that said Letters Patent is hereby corrected as shown below:

Title Page, Column 2, *Primary Examiner*, "Leon B. Crankford" should be changed to --Leon B. Lankford--

Column 8, Line 64, "bio-molecule/transfection" should be changed to --biomolecule/transfection--

Column 16, Line 16, "the solid sufface." should be changed to --the solid surface.--

Column 16, Line 23, "lamimn, pronectin," should be changed to --laminin, pronectin,--

Column 16, Line 45, "DNAIRNA" should be changed to --DNA/RNA--

Signed and Sealed this

Twentieth Day of March, 2007

JON W. DUDAS
*Director of the United States Patent and Trademark Office*